United States Patent [19]

Malyshev et al.

[11] 4,143,660
[45] Mar. 13, 1979

[54] METHOD OF SURGERY MAKING USE OF LASER EMISSION AND AN APPARATUS FOR ACCOMPLISHING SAME

[76] Inventors: Boris N. Malyshev, ulitsa Butlerova, 24, kv. 219; Viktor A. Saljuk, Teply Stan, I mikroraion, korpus 7, kv. 153; Oleg K. Skobelkin, ulitsa Vesnina, 30, kv. 27; Robert A. Toschakov, ulitsa Konstantinova, 12, kv. 31; Evgeny I. Brekhov, Rezervny proezd, 8, kv. 230, all of Moscow; Evgeny I. Egorov, Leninsky raion, poselok Dubrovsky, ulitsa Vostochnaya, 33, Moskovskaya oblast; Alexei I. Ivanov, ulitsa Blagoeva, 38, kv. 1, Kalinin, all of U.S.S.R.

[21] Appl. No.: 795,025

[22] Filed: May 9, 1977

[51] Int. Cl.² .................................................. A61B 17/36
[52] U.S. Cl. .................................. 128/303.1; 128/395; 219/121 L; 219/121 LM
[58] Field of Search ................... 128/303.1, 395–398; 219/121 L, 121 LM

[56] References Cited
U.S. PATENT DOCUMENTS

| | | | |
|---|---|---|---|
| 3,769,963 | 11/1973 | Goldman et al. | 128/395 X |
| 3,821,510 | 6/1974 | Muncheryan | 219/121 L |
| 3,865,113 | 2/1975 | Sharon et al. | 128/303.1 |
| 3,913,582 | 10/1975 | Sharon | 128/303.1 |

FOREIGN PATENT DOCUMENTS

447894  6/1975  U.S.S.R. ................................ 128/303.1

OTHER PUBLICATIONS

Hall et al., "A $CO_2$ Surgical Laser", Ann. Roy. Coll. Surg. Engl., 1971, vol. 48, pp. 181–188.

*Primary Examiner*—Lee S. Cohen
*Attorney, Agent, or Firm*—Steinberg & Blake

[57] ABSTRACT

A method whereby a hollow organ is compressed from two sides along an intended line of section after which simultaneous dissection and welding of the edges of the cavities formed is carried out by moving a focused laser beam along said line.

The degree of compressing the organ's walls is within the range from 1/5 to ½ of the initial thickness of said walls.

A device for accomplishing said method has a pair of clamping jaws drawn together or apart by means of clamps. One of the jaws serves as a guide path for a carriage, mounted on which is the exit portion of a light guide with a focusing lens. The light guide is connected with a laser. A through slot is made in one of the jaws along the line of intended section and a groove is provided on the other jaw opposite said slot. The walls of the slot and the groove have a surface reflecting the laser beam.

10 Claims, 4 Drawing Figures

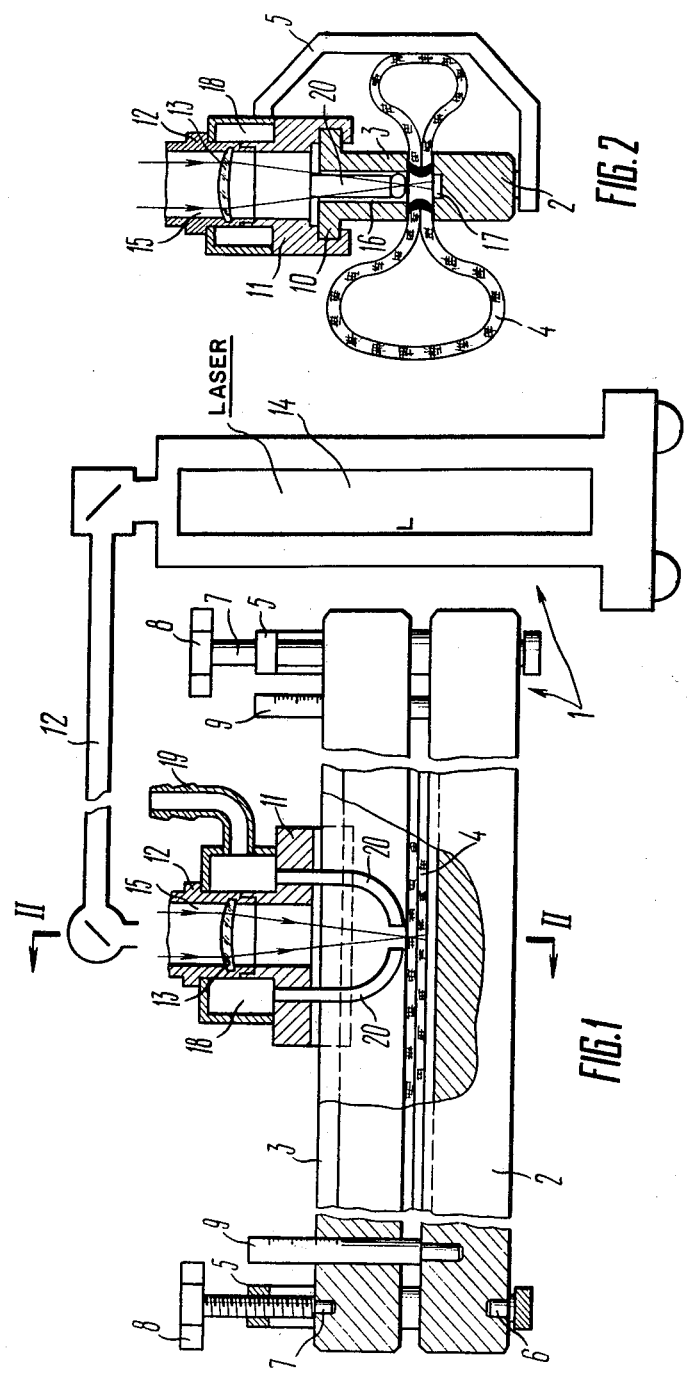

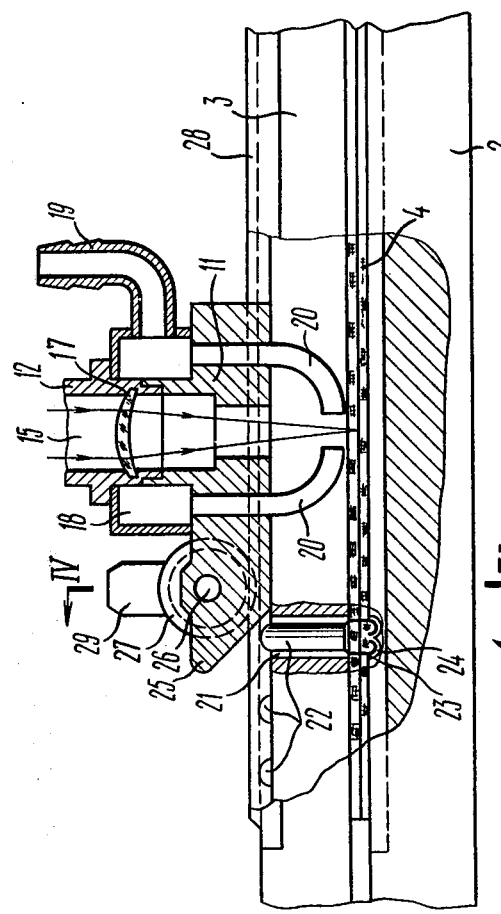

METHOD OF SURGERY MAKING USE OF LASER EMISSION AND AN APPARATUS FOR ACCOMPLISHING SAME

The present invention relates to medicine, and more particularly, to a method of surgery making use of laser emission and an apparatus for accomplishing the same. The invention can be most successfully used for conducting surgery on hollow organs, for example, the resection and formation of a stump of the urinary bladder; the formation of a tubular flap from the urinary bladder in order to form an artificial ureter; the resection of the small and large intestines; the resection and formation of a stump of the stomach; the formation of a tubular flap from a part of the greater curvature of the stomach in cases of complete and partial plastic surgery on the esophagus, and also in any other case when bloodless aseptic laser-beam dissection of an organ must be accompanied by simultaneous aseptic laser-beam welding of that organ's walls with the formation of new cavities.

As is known, the use of laser beam surgery is finding of late ever broader applications.

Usually, in prior art apparatus, a focused laser beam with power densities from $10^4$ to $10^5$ W/cm$^2$, transmitted from a laser via a light guide and focused at the light guide exit, is directed at the area to be dissected. In this case, the surgeon holds the exit portion of the light guide in his hand and moves it in a manner for the focusing point to coincide with the visually traced line of section, while visually controlling the focusing depth and travelling speed of the focusing point according to the thermophysical properties of the tissues being dissected. The depth of section in the prior art apparatus is determined by the depth of laser beam focusing (depending on the distance between the exit portion of the light guide and the surface of the organ being operated upon), the speed of the focusing point of the laser beam travelling along the intended line of section and the thermophysical properties of the tissues being dissected, whereupon the dissected tissues are joined together, for example, by means of a silk suture.

However progressive, this method of surgery making use of laser emission has a number of disadvantages.

A disadvantage of the prior art apparatus is that it provides for the dissection of tissues only, without simultaneous aseptic laser-beam welding of the organ's walls. During surgical operations on hollow organs, this results in the infection of the initially aseptic surface of the laser-beam section with the contents of the hollow organ undergoing surgery (intestine, stomach, urinary bladder, etc.) and preventing fullest utilization of the aseptic effect of laser emission. This is particularly dangerous in cases where surgery is carried out on the tissues of an organ containing large blood vessels, more than 1-1.5 mm in diameter, since the resection of the organ produces profuse hemorrhage from these vessels, and in cases when the vessels are more than 3 mm in diameter, blood may even spurt in a fountain.

Moreover, when carrying out surgery by the prior art method, healthy organs situated beneath the organ subjected to surgery may be injured, since the operating surgeon is unable to accurately control the section depth because it is impossible to correlate the depth of laser beam focusing and the travelling speed of the laser beam focusing point according to the thermophysical properties of the tissues being dissected.

At the same time, when using the prior art apparatus and method there is the danger of the laser beam damaging healthy organs situated beside the organ that is operated upon because of the natural tremor of or an accidental push to the surgeon's hand. The natural tremor of the surgeon's hand results in a wider than necessary section and the charring of its walls.

There is also the hazard of the operating medical personnel being exposed to reflected and diffuse laser emission from the auxiliary metal surgical instruments present in the operational field and from the surfaces of the tissues of the organ being operated upon.

The use of the prior art apparatus also involves the hazard of injuring the operating surgeon's eyesight by the highly intensive light radiation formed in the laser beam focusing zone as a result of the gaseous products evolving during the interaction of the laser beam with the dissected tissues when they are heated to a high temperature.

It is an object of the present invention to provide a method of surgery with use being made of laser emission that would make possible bloodless aseptic dissection of the two opposite walls of a hollow organ and simultaneous aseptic welding of the opposite dissected walls with the formation of two new cavities.

Other objects of the present invention are to considerably increase the tissue section speed in comparison with the prior art method, and also to prevent the charring of the walls of the organ being operated upon along the line of section, to guarantee the healthy organs adjacent to the operated organ against damage and to reliably protect the medical personnel against exposure both to reflected and scattered laser emission, as well as to the highly intensive light irradiation of high-temperature gaseous products evolving from the interaction of the focused powerful laser beam with the tissue being dissected.

Still another object of the present invention is to ensure the good accretion of the tissues of the resected hollow organ.

Among further objects is the provision of a surgical laser that would make it possible to effect bloodless aseptic dissection of two opposite walls of a hollow organ and simultaneous aseptic laser-beam welding of the dissected opposite walls, while increasing considerably the speed of cutting the organ's tissues in comparison to other, prior art devices, preventing the charring of the dissected walls of the organ being operated upon, and to guarantee against injury to healthy organs adjacent to the organ operated upon, and that would reliably protect medical personnel both from exposure to reflected and scattered laser radiation and exposure to the highly intensive light radiation of the high-temperature gaseous products evolving during the interaction of the focused powerful laser beam with the dissected tissue.

These and other objects are attained by that in a method of surgery on hollow organs using a focused laser beam moved along the line of intended section of a hollow organ, according to the invention, the hollow organ is preliminarily clamped on two sides so that the oppsite walls of said hollow organ touch each other along the line of intented section, after which simultaneous dissection along the compressed line and welding of the edges of the newly formed cavities is effected by moving the focused laser beam along the intended line of treatment, with the degree of compressing the walls of said hollow organ along said line being within the range of 1/5 to ½ of the initial thickness of said walls.

The proposed method makes it possible to carry out bloodless aseptic dissection of a hollow organ to be operated upon with the aid of a laser beam simultaneously with laser-beam welding of the opposite walls comprising blood vessels up to 5 mm and more in diameter.

Depending on the individual features of the hollow organs, the power of the laser beam may be within the range from 20 to 200 W, and the range of laser emission wavelengths used may vary from 0.4 to 10.6μ.

An apparatus for the implementation of the proposed method comprises a laser mounted at the entry point of a light guide at whose exit portion a focusing lens is set in accordance with the invention, clamping jaws made of a material impermeable to laser radiation and mounted with the possibility of drawing them together or apart for clamping the walls of a hollow organ on two sides along an intended line of section, and a carriage made of a material impermeable to laser radiation and mounted on a guide path, and fastened in the aforementioned carriage is the exit part of the light guide with the focusing lens, and a through-slot is made in the guide path along the line of intended section for the passage of a laser beam to the portion of the hollow organ clamped in the jaws, said slot having mirror surface walls with a high reflection coefficient reflecting the laser beam, and one of the jaws being provided with a groove in the area where the hollow organ is clamped, situated opposite the aforementioned through-slot, its surface having a high-reflection coefficient providing for diffuse scattering of laser emission, the walls of the through-slot, the groove and carriage, when the hollow organ is clamped in the jaws, forming a closed channel for the laser beam to pass there through to the secured section of the hollow organ only.

The proposed apparatus provides for the creation of a strip of compression along the intended line of section and welding of the hollow organ. The carriage, movably linked to the guide path of one of the jaws, serves to bring the focused laser beam up to the hollow organ to be operated along an accurately fixed line of section and welding, prevents the laser beam focusing point's crosswise oscillations which lead to the charring of the section's surfaces. The mirror-reflection walls of the slot in the guide path direct the laser beam to the clamped portion of the organ under surgery in case the laser beam axis does not quite coincide with the middle of the slot. The surface of the groove in one of the jaws provides for diffuse scattering of the laser emission incident thereupon, ensuring a beam power density and laser emission distribution necessary for welding. At the same time, the design of the apparatus reliably guarantees against inadvertent dissection of the patient's healthy organs and tissues adjacent to the operated organ, while excluding the exposure of medical personnel to the highly intensive light radiation from gaseous products evolving during the interaction of the powerful focused laser beam with the operated organ's tissues. On the whole, the proposed apparatus provides for rapid bloodless aseptic dissection and simultaneous welding of the two opposite walls of a hollow organ being operated upon with the formation of two new cavities on both sides of the section, at a speed 3–5 times higher than the speed of tissue section by means of prior art devices. Moreover, the welded sutures joining the newly formed cavities on both sides of the section are continuous all along their length.

It is advisable for the walls of the slot and the surface of the groove to be gold-plated.

The proposed embodiment of the apparatus can be used most effectively for the section of organs several centimaters long.

In another embodiment of the invention, the guide path has through-slots on both sides of the aforementioned through-slot, situated perpendicularly to the travelling direction of the carriage, mounted in which are tappets with metal staples, while one of the jaws opposite said tappets has grooves for clinching the staples when said tappets with staples move towards them, and the carriage is provided with a slide block for consecutively moving the tappets with the staples towards the hollow organ's clamped area.

Such a design of the apparatus ensures a two-row suture in each cavity of the dissected organ. One of the sutures is formed by the laser beam, while the second suture, passing in the immediate proximity to the first, is formed by the metal staples. Here, the height of the welded suprastaple tissue elevation is minimal, no more than 0.5 mm, while the distance between adjacent staples in the row of staples is so selected as to ensure normal blood supply in the suprastaple elevation.

The low height of the suprastaple elevation and the sufficiently large distance between adjacent staples in the row ensures speedy regeneration of the resected organ in aseptic conditions with the formation of a minimal scar without any post-operative complications. This embodiment is advisable for effecting the section of an organ longer than 10 centimeters for reinforcing the newly-made suture.

It is advisable for the apparatus to be provided with a means for measuring the compression to which the hollow organ's walls are subjected, embodied as rods with scales graduated in compression units, while one end of each rod is press-fitted into one of the clamping jaws while the rest of the rod is slide-fitted for passage through the other jaw.

Other objects and advantages of the present invention will now be described in greater detail with reference to preferred embodiments thereof, taken in conjunction with the accompanying drawings, wherein:

FIG. 1 shows a surgical laser according to the invention (longitudinal section);

FIG. 2 is a section view along line II—II of FIG. 1;

FIG. 3 shows another embodiment of the apparatus according to the invention (longitudinal section);

FIG. 4 is a section view along line IV—IV of FIG. 3.

The proposed apparatus 1 (FIGS. 1 and 2) comprises a pair of clamping jaws 2 and 3 for clamping the walls of a hollow organ 4. The jaws 2 and 3 are drawn together or apart by means of removable U-shaped clamps 5, mounted on the end portions of the jaws 2 and 3. Each clamp 5 is provided at the ends with a pin 6 and a stopper screw 7 with a handle 8, threaded through the clamp 5. The pin 6 and the end of the screw 7 are slide-fitted into respective depressions on the outer sides of the jaws 2 and 3.

Other mechanisms of similar action may be used instead of the clamps 5, for example, mechanisms with a step-by-step registration of the degree of compression.

The apparatus 1 has a means for measuring the compression of the walls of the operated organ 4. Said means is made in the form of rods 9 with scales graduated in compression units. The rods 9 are mounted at the end portions of the jaws 2 and 3, one end of each rod 9 being press-fitted into the jaw 2, while the rest of the rod 9 is slide-fitted and enters a respective opening in the jaw 3. The rods 9 also ensure that the jaws 2 and 3 move in parallel during the compression of the organ's walls.

The means for measuring the compression of the walls of the hollow organ 4 may be embodied, for example, as a piezoelectric transducer, mounted into either of the jaws 2 and 3 in the area where the hollow organ 4 is clamped and connected to a remote recording instrument.

The jaw 3 is T-shaped in section with outer lugs 10 slide-fitted into the internal slots of a carriage 11, mounted in which is the exit portion of a light guide 12 with a focusing lens 13. The entry portion of the light guide 12 is connected with a laser 14.

The jaw 2 (FIG. 2) is rectangular in cross section. However, any other cross-sectional shape of the jaws 2 and 3 is possible, for example, the jaw 3 may be of rectangular cross-section with internal guiding slots slide-fitted to external guiding lugs of the carriage 11.

An aperture 15 is made in the carriage 11 for the passage of the laser beam to the portion of the hollow organ 4 clamped between the jaws 2 and 3, opposite which the through-slot 16 is made in the jaw 3 along the line of intended section. There is a groove 17 opposite the slot 16 in the jaw 2.

The walls of the slot 16 and the groove 17 have surfaces with a high reflection coefficient, mirror-reflecting and diffuse-scattering the laser beam respectively.

The walls of the slot 16 are polished, while those of the groove 17 are matted by sand blasting. When operating with carbon dioxide, garnet lasers and a laser based on neodymium glass, the walls of the slot 16 and groove 17 have a gold plating providing for the effective reflection of the radiation incident thereupon. Here the walls of the slot 16, in the case where the laser beam axis fails to coincide with said slot's center, mirror-reflecting the laser radiation incident thereupon, perform the function of a light guide for the laser beam at the end portion of the laser beam immediately before the operated organ 4, while the walls of the groove 17 in each case perform the function of a diffuser of laser radiation.

The groove 17 is rectangular in cross-section. A semicircular or trapezoidal, or any other cross-section of said groove ensuring diffuse scattering of laser radiation can be used.

The apparatus 1 is provided with a system for removing the gaseous products evolving during the interaction of the laser beam with the tissue of the organ 4 being operated upon.

This system comprises an annular chamber 18 mounted on the carriage 11 and linked through a sleeve 19 with a means (not shown) for the aspiration of gaseous products and also tubes 20, connected with the chamber 18, passing through the slot 16 in a manner ensuring that their inlet openings are in the immediate vicinity of the laser beam's focusing point.

The tubes 20, in addition to their immediate purpose, also play the role of screens preventing the propagation of scattered laser radiation along the slot 16.

Used in our investigations were pulsed and continuous argon, carbon dioxide and neodymium garnet lasers, lasers operating on neodymium glass, as well as other lasers with laser beam powers in the range from 20 to 200 W over wave-length intervals from 0.4 to 10.6$\mu$. However, other lasers can also be used, whose selection is a matter of routine for those skilled in the art.

The light guide 12 is made as a hinged mirror system in the form of a flexible cord made of light fibers so as not to hinder the movement of the carriage 11 together with the light guide's exit portion along the jaw 3 while preserving the axis of the focused laser beam passing through the carriage 11 approximately along the center of the slot 16.

The focusing lens 13 is made of germanium when intended for operation with a carbon dioxide laser, and of optical glass when intended for operation with an argon or garnet laser and lasers with neodymium glass. In each case, the lens 13 is bloomed.

The carriage 11 and the jaws 2 and 3 are made of titanium alloys. They can also be made of stainless steel or other material impermeable to laser radiation.

Operation with the proposed apparatus proceeds as follows.

The clamping jaws 2 and 3 are set on both sides of the organ 4 to be operated, along the line intended for section, after which, by rotating the screws 7 of the clamp 5 the walls of the organ 4 are compressed. The degree of compression of the clamped walls of the organ 4, depending on the specific features of the hollow organs concerned, lies within the range of 1/5 to $\frac{1}{2}$ of the initial wall thickness and is controlled by the scale on the rod 9.

This brings about a strictly dosed increase in pressure of the interstitial biological fluid in the organ 4 in the zone of the intended section.

The carriage 11 is moved into one of its extreme positions and the system for aspirating the gaseous products evolving during the interaction of the laser beam with the tissue of the operated organ 4, is switched on. Then, the laser 14 is switched on and the carriage 11 is smoothly moved along the jaw 3. Therewith the focused laser beam passes strictly along the intended line of dissecting the tissue of the hollow organ 4. Half of the supplied laser beam power is spent mostly for dissecting the tissue of the hollow organ 4, while the rest of the emission passes towards the jaw 2 to be scattered by the diffuse reflection surface of the groove 17 and ensure mainly, simultaneous welding of the walls of said organ 4. In the process of dissecting and welding the walls of the hollow organ 4, there takes place a strictly dosed displacement and intermixing of the interstitial biological fluid of the organ 4 in the zone affected by laser emission. This is accompanied by coagulation and results in the formation of a continuous suture on both sides of the section, mechanically joining the opposite edges of the dissected organ 4 at the moment of laser beam action. Thus, two new enclosed cavities of the operated organ 4 are formed.

The walls of the slot 16, the groove 17 and the carriage 11, as the hollow organ 4 is compressed between the jaws 2 and 3, form an enclosed channel, completely isolating the surrounding space from any effect of laser radiation and gaseous products evolving during the interaction of the laser beam with the organ's tissues.

The operation over, the laser 14 is switched off together with the system for aspirating the gaseous products evolving during the operation, and the affected resected part of the hollow organ 4 is removed.

FIG. 3 shows another embodiment of the invention.

The clamping jaw 3 has additional through-slots 21 on both sides of the through slot 16 normal to the direction of travel of the carriage 11. Set in the slots 21 are tappets 22 carrying metal staples 23. Grooves 24 are made in the clamping jaw 2 opposite the tappets 22 intended for clinching the staples 23 in the clamping zone of the hollow organ 4. The carriage 11 is fitted with a slide block 25 for moving the tappets 22 with the staples 23 and carrying a shaft 26 with gears 27 which engage with teeth 28 fastened along the length of the outer surface of the jaw 3. Knobs 29 are provided with the gears 27 on the ends of the shaft 26 for rotating said shaft and moving said carriage.

When using this embodiment of the apparatus 1, the hollow organ 4 is clamped between the jaws 2 and 3 with the aid of the clamps 5 along the intended line of section. Then the system for aspirating the gaseous products and the laser 14 are switched on. By rotating knob 29 the carriage 11 is moved along the jaw 3. Herewith, the block 25 presses in succession all the tappets 22 which eject the staples 23 from the slots 21. The staples 23 pierce the walls of the operated organ 4 and are clinched against the grooves 24 of the jaw 2. The suturing of the walls of the organ 4 with the staples 23 is accompanied by the aseptic bloodless dissection and simultaneous aseptic welding of said organ's walls by the laser beam, whereby two new cavities of the organ 4 are formed, each of them with a welded suture at the side of dissecting the organ 4, reinforced by a row of the metal staples 23.

What is claimed is:

1. A method of surgery on hollow organs making use of a laser beam moving along a line of intended section of said hollow organ, comprising the steps of compressing a hollow organ from two sides so that the opposite walls of said organ join each other along the intended line of section, the degree of compression of said walls of the hollow organ along said section line being within the range from 1/5 to ½ from the initial thickness of its wall; then simultaneously dissecting said organ along the intended line of section and welding the edges of the formed cavities of said hollow organ through the movement of a focused laser beam along the line of section.

2. A method as claimed in claim 1, wherein the power of the laser beam is within the range of from 20 to 200 W, and the range of the wavelengths used is from 0.4 to 10.6μ.

3. A surgical laser for implementing a method of surgery making use of a focused laser beam moved along an intended line of dissection of a hollow organ, comprising a pair of clamping jaws made of a material impermeable to laser radiation means for adjustably moving the jaws together and apart for compressing the walls of the hollow organ from two sides along an intended line of section; said jaws being mounted on said means for moving; one of said jaws including a guide path thereon; a carriage movable mounted on the guide path provided on said one of said jaws and made of a material impermeable to laser radiation, said carriage including a through-slot; a laser with a light guide, the entry section of said light guide being joined to the laser and its exit section including a focusing lens and being provided in said through-slot and a through-slot in said one of said jaws including said guide path and clamping surface for the passage of the laser beam to the area of said hollow organ clamped in said jaws, the walls of said jaw through-slot having a mirror surface with a high reflection coefficient, reflecting the laser beam, the other of said jaws provided with a groove on the clamping surface thereof in the area of compressing said hollow organ and situated opposite said jaw through-slot, and having a diffuse-scattering surface with a high-reflection coefficient; said walls of said through-slots and groove defining, upon the compression of said hollow organ in said jaws, a closed channel for the passage of the laser beam exclusively to said compressed area of said hollow organ.

4. A surgical laser as claimed in claim 3, wherein the walls of said jaw through-slot and the surface of said groove are gold-plated.

5. A surgical laser as claimed in claim 3, wherein additional through-slots are provided in said one of said jaws at sustantially right angles to the guide path on both sides of said jaw through-slot and situated at a right angle to the direction of the travel of the carriage, each of said additional through-slots having; mounted therein tappets with metal staples, and the other one of the jaws having groove means formed in opposed relationship to each of said tappets for clinching the staples as the tappets with the staples travel towards them, the carriage being provided with a slide block for movement therewith adapted to operatively engage and consecutively move said tappets with the staples towards the compressed area of the hollow organ.

6. A surgical laser as claimed in claim 5, wherein the walls of said jaw through-slot and the surface of said groove are gold-plated.

7. A surgical laser as claimed in claim 5, having a means for measuring the compression of the hollow organ's walls.

8. A surgical laser as claimed in claim 7, wherein the means for measuring the compression of the hollow organ's walls is made in the form of rods with scales graduated in compression units, one end of each rod being press-fitted into one of the jaws with the remaining part of the rod being slide-fitted into and passing through the other jaw.

9. A surgical laser as claimed in claim 3, having a means for measuring the compression of the hollow organ's walls.

10. A surgical laser as claimed in claim 9, wherein the means for measuring the compression of the hollow organ's walls is made in the form of rods with scales graduated in compression units, one end of each rod being press-fitted into one of the jaws, the remaining part of the rod being slide-fitted into and passing through the other jaw.

* * * * *